United States Patent
Boyce et al.

(10) Patent No.: US 8,758,438 B2
(45) Date of Patent: Jun. 24, 2014

(54) IMPLANT FOR ORTHOPEDIC APPLICATIONS

(75) Inventors: Todd M Boyce, Collierville, TN (US); Lawrence A. Shimp, Burlington, WI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 299 days.

(21) Appl. No.: 10/433,523

(22) PCT Filed: Dec. 7, 2001

(86) PCT No.: PCT/US01/47644
§ 371 (c)(1),
(2), (4) Date: Jun. 4, 2003

(87) PCT Pub. No.: WO02/056800
PCT Pub. Date: Jul. 25, 2002

(65) Prior Publication Data
US 2004/0024457 A1  Feb. 5, 2004

Related U.S. Application Data

(60) Provisional application No. 60/254,378, filed on Dec. 8, 2000.

(51) Int. Cl.
*A61F 2/08* (2006.01)
(52) U.S. Cl.
USPC ..................... 623/13.17; 623/13.19
(58) Field of Classification Search
USPC ...................... 623/13.17, 13.18, 13.19, 23.63
See application file for complete search history.

(56) References Cited

U.S. PATENT DOCUMENTS

| | | | |
|---|---|---|---|
| 3,316,557 A * | 5/1967 | Liebig | 623/1.38 |
| 3,625,811 A * | 12/1971 | Okamura | 162/2 |
| 4,089,071 A | 5/1978 | Kalnberz et al. | |
| 4,202,055 A | 5/1980 | Reiner et al. | |
| 4,294,753 A | 10/1981 | Urist | |
| 4,713,076 A | 12/1987 | Draenert | |
| 4,877,864 A | 10/1989 | Wang et al. | |
| 4,902,508 A | 2/1990 | Badylak et al. | |
| 4,969,904 A * | 11/1990 | Koch et al. | 623/23.54 |
| 4,976,738 A * | 12/1990 | Frey et al. | 623/23.54 |
| 5,013,649 A | 5/1991 | Wang et al. | |
| 5,037,442 A * | 8/1991 | Wintermantel et al. | 623/23.16 |

(Continued)

FOREIGN PATENT DOCUMENTS

| | | |
|---|---|---|
| EP | 0 306 018 | 3/1989 |
| EP | 0306018 | 3/1989 |

(Continued)

OTHER PUBLICATIONS

International Search Report of App. No. PCT/US01/47644, Jul. 2002.

(Continued)

*Primary Examiner* — Paul Prebilic
(74) *Attorney, Agent, or Firm* — Sorell Lenna & Schmidt LLP

(57) ABSTRACT

An implant for orthopedic applications includes a quantity of flexible, elongated elements at least some of which possess connective tissue-healing activity, the elongated elements being arranged in substantially common alignment along their longitudinal axis.

1 Claim, 2 Drawing Sheets

(56) References Cited

U.S. PATENT DOCUMENTS

| | | | |
|---|---|---|---|
| 5,053,049 A | 10/1991 | Campbell | |
| 5,073,373 A | 12/1991 | O'Leary et al. | |
| 5,092,887 A | 3/1992 | Gendler | |
| 5,106,478 A | 4/1992 | Wozney et al. | |
| 5,108,922 A | 4/1992 | Wang et al. | |
| 5,116,738 A | 5/1992 | Wang et al. | |
| 5,171,273 A | 12/1992 | Silver et al. | |
| 5,187,076 A | 2/1993 | Wozney et al. | |
| 5,243,038 A | 9/1993 | Ferrari et al. | |
| 5,263,984 A | 11/1993 | Li et al. | |
| 5,314,476 A | 5/1994 | Prewett et al. | |
| 5,366,875 A | 11/1994 | Wozney et al. | |
| 5,378,469 A | 1/1995 | Kemp et al. | |
| 5,393,594 A | 2/1995 | Koyfman et al. | |
| 5,405,390 A | 4/1995 | O'Leary et al. | |
| 5,507,810 A | 4/1996 | Prewett et al. | |
| 5,507,813 A | 4/1996 | Dowd et al. | |
| 5,522,841 A | 6/1996 | Roby et al. | |
| 5,552,454 A | 9/1996 | Kretschmann et al. | |
| 5,607,269 A | 3/1997 | Dowd et al. | |
| 5,624,463 A | 4/1997 | Stone et al. | |
| 5,652,056 A * | 7/1997 | Pepin | 428/364 |
| 5,705,181 A | 1/1998 | Cooper et al. | |
| 5,711,960 A | 1/1998 | Shikinami | |
| 5,837,752 A | 11/1998 | Shastri et al. | |
| 5,899,939 A | 5/1999 | Boyce | |
| 5,962,427 A | 10/1999 | Goldstein et al. | |
| 5,989,894 A | 11/1999 | Lewis et al. | |
| 6,048,964 A | 4/2000 | Lee et al. | |
| 6,090,998 A | 7/2000 | Grooms et al. | |
| 6,123,731 A | 9/2000 | Boyce et al. | |
| 6,124,001 A | 9/2000 | Sugita et al. | |
| 6,132,871 A | 10/2000 | Andrews et al. | |
| 6,183,498 B1 | 2/2001 | Devore et al. | |
| 6,294,041 B1 | 9/2001 | Boyce | |
| 6,294,187 B1 | 9/2001 | Boyce et al. | |
| 6,333,029 B1 * | 12/2001 | Vyakarnam et al. | 424/93.1 |
| 6,376,573 B1 | 4/2002 | White et al. | |
| 6,440,444 B2 | 8/2002 | Boyce | |
| 6,441,073 B1 | 8/2002 | Tanaka et al. | |
| 6,696,073 B2 | 2/2004 | Boyce | |
| 6,843,807 B1 | 1/2005 | Boyce | |
| 6,933,328 B2 | 8/2005 | Schacht | |
| 7,270,813 B2 | 9/2007 | Shimp | |
| 7,291,345 B2 | 11/2007 | Winterbottom | |
| 2002/0107570 A1 * | 8/2002 | Sybert et al. | 623/13.17 |
| 2003/0045942 A1 | 3/2003 | Lai et al. | |
| 2003/0114552 A1 | 6/2003 | Schacht | |
| 2003/0143258 A1 | 7/2003 | Knaack | |
| 2003/0236573 A1 | 12/2003 | Evans et al. | |
| 2004/0024457 A1 | 2/2004 | Boyce | |
| 2004/0034434 A1 | 2/2004 | Evans et al. | |
| 2004/0064193 A1 | 4/2004 | Evans et al. | |
| 2004/0138758 A1 | 7/2004 | Evans et al. | |
| 2004/0146543 A1 | 7/2004 | Shimp | |
| 2004/0180344 A1 | 9/2004 | Morris et al. | |
| 2005/0027033 A1 | 2/2005 | Knaack | |
| 2005/0209696 A1 | 9/2005 | Lin | |
| 2005/0251267 A1 | 11/2005 | Winterbottom | |
| 2005/0281856 A1 | 12/2005 | McGlohorn et al. | |
| 2005/0283255 A1 | 12/2005 | Geremakis | |
| 2006/0015184 A1 | 1/2006 | Winterbottom | |
| 2006/0216323 A1 | 9/2006 | Knaack | |
| 2007/0154563 A1 | 7/2007 | Behnam | |
| 2007/0178158 A1 | 8/2007 | Knaack | |
| 2007/0191963 A1 | 8/2007 | Winterbottom | |
| 2007/0233272 A1 | 10/2007 | Boyce | |
| 2008/0009955 A1 | 1/2008 | Shimp | |
| 2008/0063684 A1 | 3/2008 | Winterbottom | |
| 2008/0069852 A1 | 3/2008 | Shimp | |
| 2008/0187260 A1 | 8/2008 | Schubert | |
| 2008/0188945 A1 | 8/2008 | Boyce | |
| 2009/0260935 A1 | 10/2009 | Avadhany | |
| 2009/0287308 A1 * | 11/2009 | Davis et al. | 623/13.12 |

FOREIGN PATENT DOCUMENTS

| | | | |
|---|---|---|---|
| EP | 0485986 | 11/1991 | |
| EP | 0 485 986 | 5/1992 | |
| EP | 0485986 | 5/1992 | |
| EP | 0943346 | 11/1997 | |
| WO | WO 93/00432 | 1/1993 | |
| WO | WO 94/26892 | 11/1994 | |
| WO | WO 94/26893 | 11/1994 | |
| WO | WO 98/44965 | 10/1998 | |
| WO | WO 99/21515 | 5/1999 | |
| WO | WO-99/39757 | 8/1999 | |
| WO | WO 9939757 * | 8/1999 | A61L 27/00 |
| WO | WO 00/45747 | 8/2000 | |
| WO | WO 00/50102 | 8/2000 | |
| WO | WO 02/056800 | 7/2002 | |
| WO | WO 03/030956 | 4/2003 | |
| WO | WO 2004/014452 | 2/2004 | |
| WO | WO 2004/032988 | 4/2004 | |
| WO | WO 2004/053112 | 6/2004 | |
| WO | WO 2004/069890 | 8/2004 | |
| WO | WO 2005/062868 | 7/2005 | |
| WO | WO 2005/065396 | 7/2005 | |
| WO | WO 2005/072656 | 8/2005 | |
| WO | WO 2005/074850 | 8/2005 | |
| WO | WO 2005/107651 | 11/2005 | |
| WO | WO 2007/084609 | 7/2007 | |
| WO | WO 2007/084610 | 7/2007 | |
| WO | WO 2007/084725 | 7/2007 | |
| WO | WO 2008/086563 | 7/2008 | |

OTHER PUBLICATIONS

Giraud-Guille, "Twisted Plywood Architecture of Collagen Fibrils in Human Compact Bone Osteons", *Calcif. Tissue Int.*, 42: 167-80, 1988.

Horan, et al., "Yarn design for functional tissue engineering", *Journal of Biomechanics*, 39: 2232-40, Sep. 22, 2005.

Nalla, et al., "Role of microstructure in the aging-related deterioration of the toughness of human cortical bone", *Materials Science & Engineering*, C 26(8): 1251-60, Oct. 3, 2005.

Rho, et al., "Mechanical properties and the hierarchical structure of bone", *Medical Engineering & Physics*, 20: 92-102. Mar. 1998.

Sampath, et al., "Dissociative extraction and reconstitution of extraxellular matrix componets involved in local bone differentiation", *Proc. Natl. Acad. Sci. USA*, 78(12): 7599-7603, 1981. Dec. 1981.

Trębacz, et al., "Thermal stabilization of collagen molecules in bone tissue", *Int'l Journal of Biological Macromolecules*, 37: 257-62, Dec. 2005.

Woo, et al., "Anatomy, Biology, and Biomechanics of Tendon, Ligament, and Meniscus", *Orthopaedic Basic Science*, Ch. 2: 45-87, 1994.

International Search Report, PCT/US01/47644, Jul. 2002.

\* cited by examiner

IMPLANT FOR ORTHOPEDIC APPLICATIONS

BACKGROUND OF THE INVENTION

1. Field of the Invention

The present invention relates to an implant which is useful for a variety of orthopedic applications. More particularly, the present invention relates to an implant useful for treating bone injuries, defects, etc., such as spinal disorders for which spinal fusion is indicated and the repair or replacement of ligaments, tendons and/or cartilage.

2. Description of Related Art

A variety of implants having application as artificial bone, ligaments, tendons, cartilage, and the like, are known. U.S. Pat. No. 4,089,071 describes a material for making bone endoprostheses featuring a laminated structure of net-like construction. U.S. Pat. No. 5,092,887 describes an elongated artificial ligament made from demineralized bone which is said to exhibit compliant elasticity and high longitudinal strength. U.S. Pat. No. 5,263,984 describes a prosthetic ligament made up of a quantity of substantially aligned, elongated filaments each of which is a biocompatible, resorbable fibril made, e.g., of collagen, elastin, reticulin, cellulose, algenic acid or chitosan. U.S. Pat. No. 5,711,960 describes an implant, useful inter alia, as a prosthetic or filling for a defective bone, which utilizes, as a base material, a biocompatible bulk structure of a three-dimensionally woven or knitted fabric of organic fibers whose surfaces have been biologically activated or inactivated. U.S. Pat. No. 6,090,998 describes a bone implant, useful for the repair or replacement of ligaments, tendons and joints, which includes at least one mineralized segment and at least one demineralized, flexible segment.

Developing cells are known to migrate along surfaces. When the surface is oriented, the potential exists to somewhat control the direction of growth. It has been observed by the inventors in animal studies that fibrous materials provide better osteoconduction than particle based materials. Therefore, a material which guides the formation of new tissue would have the ability to direct osteoconduction as well as other types of tissue growth. Such a material, by directing the formation of new tissue, would be expected to demonstrate improved strengthening effects. In addition, a fibrous implant, unlike particle-based implants, would tend to remain where placed in the body and would resist being dislodged therefrom.

SUMMARY OF THE INVENTION

It is an object of the present invention to provide an implant which is useful for the treatment of defects and injuries of bone, ligaments, tendons and cartilage.

It is a further object of the invention to provide an implant that is biocompatible and will not be rejected by the host.

It is still a further object of the invention to provide an implant for various orthopedic applications which can be combined with one or more separate therapeutically useful substances or structurally useful biomaterials, e.g., titanium wire or mesh.

By way of attaining these and other objects of the invention, an implant is provided which comprises a quantity of flexible, elongated elements at least some of which possess connective tissue-healing activity, the elements being arranged in substantially common alignment along their longitudinal axis.

Significant advantages of the implant flow from the substantial alignment of the elongated members along their longitudinal, or major, axis. Thus, when the elongated members are thus aligned to provide, e.g., a woven or braided structure, the result is an implant which is generally stronger than the elongated members from which the implant is made. In addition, the implant can be made to possess dimensions which could not be achieved with naturally occurring implant materials such as whole bone sections.

Still another advantage resides in the ability of a particular implant to utilize combinations of different materials as sources for its elongated members. Selection from among a large variety of such materials expands the range of biological and/or mechanical properties that can be built into a given implant.

The implant of the present invention, unlike conventional metallic implants, will not stress shield the bone at the implant site. Therefore, any tendency for already existing healthy bone to be resorbed at the implant site will be reduced. In addition, unlike metallic implants, the implant of this invention will not interfere with the use of postoperative plain film X-rays, MRI or CT scans.

The expression "elongated elements" refers to the structural units constituting the implant of this invention and having the appearance of filaments, threads, strips and similarly elongated configurations. The elongated elements can be separate units for their entire length or two or more of the elements can have a common point of attachment, e.g., as shown in the implant of FIG. 1a.

The term "biocompatible" and expressions of like import shall be understood to mean the absence of unacceptable detrimental biological response, e.g., stimulation of a severe, long-lived or escalating biological response to an implant and is distinguished from a mild, transient inflammation which accompanies implantation of essentially all foreign objects into a living organism and is also associated with the normal healing response. Thus, materials which alone in appropriate quantities are generally considered nonbiocompatible can be considered biocompatible within the aforestated meaning if present in small enough quantities such that they do not elicit a significant level of undesirable or detrimental tissue response.

The expression "connective tissue-healing activity" refers to the ability of the implant of the invention to participate in the repair, regeneration, healing, etc., of connective tissue, e.g., bone, ligament, tendon or cartilage, by one or more mechanisms including chondrogenesis, osteoinduction, osteogenesis and osteoconduction.

The term "chondrogenic" as used herein shall be understood to refer to the ability of a material or substance to induce or otherwise participate in the formation of cartilage.

The term "osteoinductive" as used herein shall be understood to refer to the ability of a material or substance to recruit cells from the host which have osteogenic potential and the ability to form ectopic bone.

The term "osteogenic" as used herein shall be understood to refer to the ability of a material or substance to induce new bone formation via the participation of living cells from within the substance.

The term "osteoconductive" as used herein shall be understood to refer to the ability of a material or substance or material to provide surfaces that are receptive to the growth of new host bone.

The expression "substantially common alignment" refers to the relative orientation of the elongated elements constituting the implant and includes woven, knitted, braided, or twisted arrangements of individual elements as well as subassemblies of several elongated elements formed into yarns, twines, strands, etc.

The term "resorbable" refers to the ability of materials to be broken down by normal biochemical and/or physical processes such as erosion, dissolution, etc.

The term "remodeling" refers to the process whereby materials are broken down and then replaced by host tissue, e.g., by resorption of existing bone tissue by osteoclasts and formation of new bone tissue by osteoblasts.

Other advantages of the present invention will become apparent to one skilled in the art from the following written description and accompanying figures.

BRIEF DESCRIPTION OF THE DRAWINGS

In FIG. 1A, an elongated section of bone is cut or machined to provide three relatively wide elongated elements arranged in a braided pattern. In FIG. 1B, the elongated section of bone is cut or machined to provide elongated elements which are formed into yarns with the yarns subsequently being formed into braids. FIGS. 1C-1E schematically depict demineralized bone strips arranged into various other structures. As shown, the implants are substantially longer than they are wide, and substantially longer than they are thick.

DETAILED DESCRIPTION OF THE INVENTION

The implant of this invention is fabricated in whole or in part from flexible elongated elements, advantageously biocompatible in character, e.g., connective type tissues obtained from human and animal tissues and natural and synthetic fibers including, but not limited to, demineralized bone, tendon, ligament, collagen, elastin, reticulin, cellulose, alginic acid, chitosan, small intestine submucosa, silk, nonresorbable and resorbable synthetic polymeric fibers, and the like. The elongated elements can also be obtained from microorganisms, particularly genetically engineered microorganisms such as yeast and bacteria and genetically engineered eucaryotic cell cultures such as Chinese hamster ovary cell lines, HeLa cells, etc. For example, U.S. Pat. Nos. 5,243,038 and 5,989,894, each of which is incorporated herein by reference, describes the expression of spider silk protein, collagen proteins, keratins, etc., using genetically engineered microorganisms and eucaryotic cell lines.

When the elongated elements are fabricated in whole or in part from tissues such as bone, tendon, ligament, small intestine submucosa tissue, and the like, such tissues are first processed to remove any blood and debris that may be associated therewith and the tissues are then sterilized employing routine procedures such as those described below. The processed tissues are then fashioned into elongated elements whose dimensions are selected so that when assembled into the implant, the latter will have sufficient length to span, and be affixed to, the implant site, and sufficient width and thickness to impart such desirable properties as toughness, flexibility and strength to the implant.

Figure 1A:
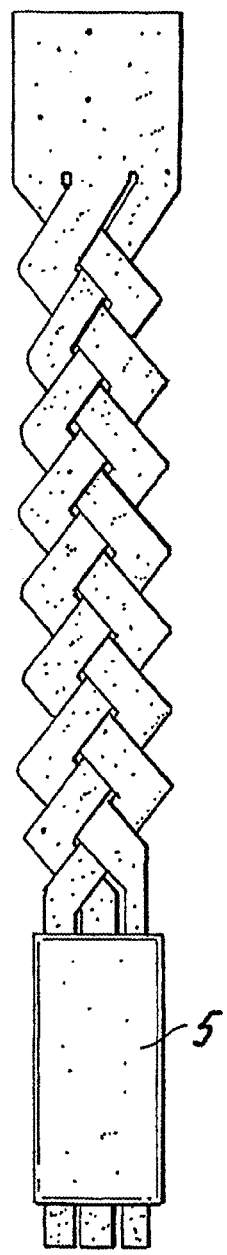
FIGS. 1A-1E are diagrammatic representations of implants in accordance with the present invention.
Figure 1B:
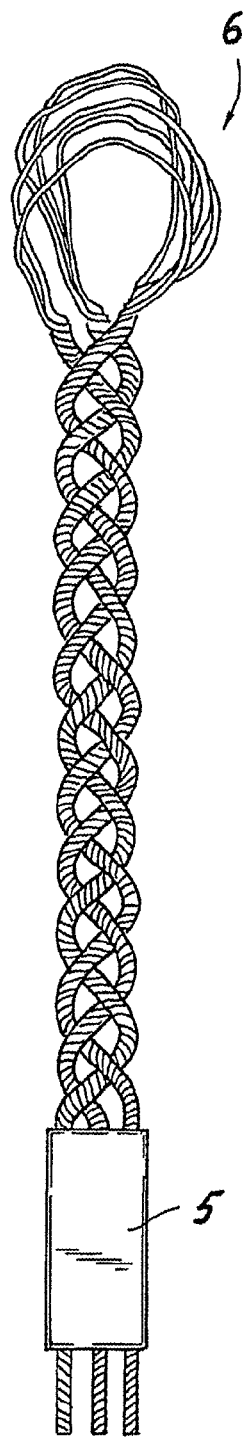
Figure 1C:
Figure 1D:
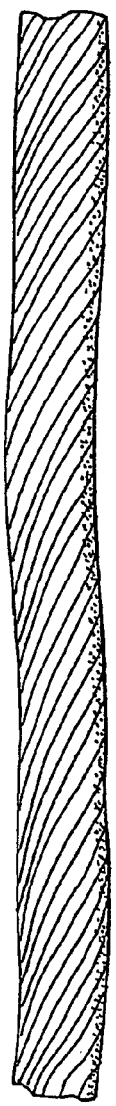
Figure 1E:
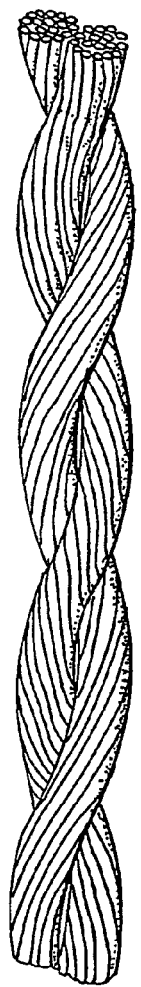

The elongated tissue elements can be formed into implants having a variety of configurations such as those shown in FIGS. 1A-1E. For example, FIG. 1A schematically depicts one embodiment in which a sheet of bone is further cut or machined into three elongated elements of about the same width which are then formed into a braid. FIGS. 1B-1E schematically depict other embodiments wherein a section of bone is cut or machined to provide a quantity of elongated elements which are then assembled into the implants shown.

The overall dimensions of the flexible elongated elements making up the implant of this invention can vary widely depending on the dimensions of the site to which the implant is to be affixed. Typically, these dimensions will range from about 1 cm to about 1 meter in length, preferably from about 3 cm to about 8 cm in length, from about 0.5 mm to about 30 mm in thickness, preferably from about 2 mm to about 10 mm in thickness, and from about 0.05 mm to about 150 mm in width, preferably from about 2 mm to about 10 mm in width.

While fully mineralized bone, tendon, ligament, small intestine submucosa, collagen tissues, etc., in themselves are not particularly osteoinductive, such tissues can be rendered osteoinductive by subjecting the tissue to various procedures and/or incorporating one or more osteoinductive substances in the tissues. For example, the mineral content of bone tissue can be reduced by demineralization, a process which results in the removal of the inorganic components of the bone, largely hydroxyapatite, which gives bone its characteristic rigidity and structural properties. The resultant demineralized bone is both flexible and osteoinductive. Bone, tendon, ligament, small intestine submucosa and collagen tissues can be rendered osteoinductive by association with, or incorporation of, various osteoinductive materials which include, but are not limited to, growth factors such as bone-derived growth factor, bone morphogenic proteins, osteogenic proteins such as OP-1, hormones, growth hormone, platelet derived growth factor (PDGF), insulin-like growth factors (IGF-1)(IGF-2), DNA-encoding various therapeutic agents such as growth factors and hormones, gene activated matrix, i.e., a matrix containing DNA encoding therapeutic proteins utilized to promote cell growth, which in turn, promote DNA transfer into repair cells, demineralized bone in the form of particles, powder, gel, liquid, etc, ceramic powders of calcium phosphate and/or apatite (hydroxyapatite) and bioglasses. Bone morphogenic proteins can be obtained from Genetics Institute, Inc. (Cambridge, Mass.) and Stryker Corporation (Kalamazoo, Mich.) and may also be prepared by one skilled in the art as described, e.g., in. U.S. Pat. Nos. 5,187,076, 5,366,875, 4,877,864, 5,108,922, 5,116,738, 5,013,649, 5,106,748, WO93/00432, WO94/26893 and WO94/26892, each of which is incorporated by reference herein. All osteoinductive factors are contemplated whether they are obtained as above or isolated from bone or other human or animal tissues. Methods for isolating bone morphogenic protein from bone are described, e.g., in U.S. Pat. No. 4,294,753, incorporated herein by reference. Methods of preparing demineralized bone powder, demineralized bone particles, and demineralized bone in the form of a liquid, and demnineralized bone in the form of a gel are well known in the art as described, e.g., in U.S. Pat. Nos. 5,314,476, 5,507,813, 5,073, 373, and 5,405,390, respectively, each of which is incorporated by reference herein. Methods of preparing osteogenic proteins, such as OP-1 are described, e.g., in U.S. Pat. No. 6,048,964 which is incorporated by reference herein. Methods of transferring DNA-encoding therapeutic proteins into repair cells utilizing gene activated matrix are described, e.g., in U.S. Pat. No. 5,962,427 which is incorporated by reference herein. Methods of preparing ceramic powders of calcium phosphate and/or hydroxyapatite are described, e.g., in U.S. Pat. Nos. 4,202,055 and 4,713,076, each of which is incorporated by reference herein. Methods of preparing bioglasses are described, e.g., in WO 98/44965, which is incorporated by reference herein. Suitable methods of incorporation or association of such osteogenic factors include coating, immersion saturation, packing, spraying, e.g., plasma spraying, injecting into the bone tissue, etc.

When desirable, e.g., for preparing an implant suitable for soft tissue repair, the flexible elongated elements constituting the implant can be treated to so as to reduce their osteoinductive properties. For example, demineralized bone is known to possess osteoinductive characteristics. When desirable, such characteristics can be reduced or eliminated by appropriate further treatment. For example, the osteoinductive proteins in the demineralized bone can be denatured, and thus deactivated, by reaction with, for example, a chemical denaturant such as glutaraldehyde or formaldehyde. Demineralized bone treated in this way is known to support the formation of fibrous tissue and as such, exhibits connective tissue-healing activity although, of course, through a mechanism other than that of osteoinduction. The degree of denaturation can be controlled to give the desired physical and biological properties. Other denaturation methods include irradiation and thermal treatment. Alternatively, osteoinductive proteins can be extracted from the demineralized bone employing extractants such as guanidine hydrochloride.

Implants of this invention containing bone or other tissue material can be further treated by tanning or other means known in the art to reduce their antigenicity. For example, glutaraldehyde treatment (see U.S. Pat. No. 5,053,049 which is incorporated by reference herein) can be used for this purpose.

Employing a milling technique, elongated bone elements ranging in median length from about 2 up to about 200 mm or more (as in the case of the long bones), in median thickness from about 0.05 to about 2 mm and in median width from about 1 to about 20 mm can be readily obtained. Another procedure for obtaining the elongated bone particles herein, particularly useful for elements of bone of up to about 100 mm in length, is the bone milling apparatus described in U.S. Pat. No. 5,607,269 the contents of which are incorporated by reference herein. Use of this apparatus results in the production of long, thin bone strips which tend to curl lengthwise into tube-like structures.

Depending on the procedure employed for producing the elongate bone elements, one can obtain a mass of bone elements containing at least about 60 weight percent, preferably at least about 70 weight percent, and most preferably at least about 80 weight percent of bone elements possessing a median length of from about 2 to about 200 mm or more and preferably from about 10 to about 100 mm, a median thickness of from about 0.05 to about 2 mm and preferably from about 0.2 to about 1 mm and a median width of from about 1 mm to about 20 mm and preferably from about 2 to about 5 mm. These bone elements can possess a median length to median thickness ratio of at least about 50:1 up to about 500:1 or more and preferably from about 50:1 to about 100:1 and a median length to median width ratio of from about 10:1 to about 200:1 and preferably from about 50:1 to about 100:1.

If desired, the mass of elongated bone elements can be graded into different sizes to reduce or eliminate any less desirable size(s) of elements which may be present. In overall appearance, the elongated bone elements can be described as filaments, fibers, threads, slender or narrow strips, etc. As already noted and depending on the manner in which they are produced, these elongated elements may have a tendency to curl lengthwise into tube-like structures.

When the implant of this invention is fabricated from bone, the bone is preferably chosen from a cortical bone such as the femur, tibia, fibula, radius or ulna. The bone elements can be obtained from cortical, cancellous and/or corticocancellous bone which can be of autogenous, allogenic and/or xenogeneic origin: Porcine bone is a particularly advantageous type of xenogeneic bone tissue which can be used as a source for the elongated bone elements of this invention.

Following the shaving, milling or other technique whereby they are obtained, the elongated bone elements are subjected to demineralization in order to reduce their inorganic content and, as may be necessary for a particular embodiment, to increase their flexibility. Demineralization of the bone elements will ordinarily result in elongated elements of slightly smaller dimensions than those of the mineralized elements from which they were obtained.

The elongated bone elements can be demineralized in accordance with known and conventional procedures. The mineral content of bone can be removed to varying degrees. The term "fully demineralized" as it applies to an elongated bone element refers to a bone element possessing less than about 8, preferably less than about 1, weight percent of its original inorganic mineral content. The term "partially demineralized" as it applies to an elongated bone element means that the bone element possesses from about 8 to about 90 weight percent of its original inorganic mineral content. The term "superficially demineralized" as it applies to an elongated bone element refers to a bone element possessing at least 90 weight percent of its original inorganic mineral content. The term "demineralized" as it applies to an elongated bone element includes any one or combination of the foregoing types of demineralized elongated bone elements. The use of superficially, partially or fully demineralized bone can, in some embodiments, be particularly advantageous since demineralized bone exhibits considerably greater initial osteoinductive activity than fully mineralized bone.

Demineralization can precede or follow the cutting, slicing, milling, etc., of the bone into elongated elements. Thus, a whole section of bone, e.g., a diaphyseal shaft, can first be demineralized to the extent desired after which it is machined to provide the individual elongated bone elements. Alternatively, the whole bone can be subdivided into individual elongated bone elements which are thereafter demineralized to the desired level.

Of course it will be understood by those skilled in the art that the bone elements will be demineralized to such an extent that they can be worked to form the implant of the invention herein. Therefore, when the bone elements are of such size as to be relatively inflexible prior to demineralization, they can be demineralized to the point where they are flexible and capable of being worked, e.g., woven, braided, spun, etc. When bone elements are of such dimensions that they are relatively flexible prior to demineralization, a lesser degree of demineralization may be appropriate. The extent of demineralization necessary to obtain a bone element that is workable can be readily determined by one skilled in the art employing routine experimentation.

Demineralization of the elongated bone elements can be conducted using conventional procedures that are well known in the art, e.g., subjecting the bone section to strong acids such as hydrochloric acid as described, e.g., in Reddi et al., *Proc. Nat. Acad. Sci.* 69:1601-5 (1972), incorporated herein by reference. The extent of demineralization is a function of the strength of the acid solution, the shape of the bone and the duration of the demineralization treatment. Reference in this regard may be made to Lewandrowski et al., *J. Biomed. Materials Res.* 31:365-372 (1996), incorporated herein by reference.

In a preferred demineralization procedure, the elongate bone elements are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. The preferred concentration range of the defatting solution is from about 60 to about 85 weight percent alcohol and most preferably about 70 weight percent alcohol. Following defatting, the bone elements are immersed in acid over time to effect their demineralization. Acids which can be employed in this step include inorganic acids such as hydrochloric acid and organic acids such as peracetic acid. Generally, the concentration of inorganic acid utilized to achieve demineralization is from about 0.1N to about 2N and more preferably from about 0.2 N to about 1.0 N. The time of exposure to the acid is increased for lower acid concentrations and decreased for the higher acid concentrations. After acid treatment, the demineralized bone elements are rinsed with sterile water for injection to remove residual amounts of acid and thereby raise the pH.

The wet demineralized bone elements can then be immediately formed into the implant of this invention in accordance using methods well known in the art, e.g., those described in U.S. Pat. No. 5,263,984 the contents of which are incorporated by reference herein, or stored under aseptic conditions, advantageously in a lyophilized state, for processing at a later time.

When the bone elements are shorter than the desired length of the implant, they can be combined with fibers and/or other materials such that a final implant of the desired length is produced. For example, the relatively short bone elements can be combined with other materials in a known manner, e.g., to form a spun yarn, which can then be woven to form the implant of the invention. Thus, the short bone elements can be combined with demineralized bone elements of greater length or with bioresorbable polymeric fibers, ceramic or glass fibers, or biocompatible metal fibers of suitable length to produce a composite yarn which can then be woven using standard techniques to produce the implant of the invention.

Optionally, the short bone elements can be combined with bioresorbable thermoplastic material that is formed into spun-bonded and/or non-woven fabrics. For example, after the bioresorbable thermoplastic material has been formed into a first web, the short bone elements can be applied to the first web and then sandwiched with a second web to form a controlled elastic composite material. The methods of forming a composite material disclosed in U.S. Pat. Nos. 6,124,001 and 6,132,871 are incorporated by reference herein and are suitable for forming the aforedescribed elastic composite.

In one embodiment, the bone comprises a plurality of elongated bone elements. Typically, the bone is obtained from a suitable vertebrate and processed by conventional techniques to remove blood and lipid from the bone. The bone can then be cut into elongated sections by techniques which are well known in the art e.g., longitudinally cutting an entire bone section or relatively large portion of bone into elongated sections using a band saw or a diamond-bladed saw, or milling the surface of an entire bone or relatively large portion of bone. Alternatively, the bone can be cut by making transverse cuts to prepare a bone section of the appropriate length, followed by longitudinal cuts using a band saw or a diamond cut saw. As stated above, elongated elements of bone can be further cut or machined into a variety of different shapes. In overall appearance the elongated bone elements can be described as narrow or thick strips, segments, sheets, rods, struts, etc. The elongated elements can be further processed to remove residual blood and lipid residue.

Prior or subsequent to cutting or milling of the bone into elongated elements, the bone is preferably demineralized to reduce its inorganic content utilizing the defatting/demineralization procedure described herein above. After acid treatment, the elongated bone elements are rinsed with sterile water for injection, buffered with a buffering agent to a final predetermined pH and then finally rinsed with water for injection to remove residual amounts of acid and buffering agent or washed with water to remove residual acid and thereby raise the pH.

In a particularly useful embodiment, the elongated bone elements can be segmentally demineralized employing procedures known in the art as described, e.g., in U.S. Pat. No. 6,090,998, which is incorporated herein by reference.

Alternatively, the end portions of the elongated bone elements can be surface demineralized by any convenient method. For example, the bone elements can be subjected to demineralization conditions for a period of time sufficient to demineralize only their surfaces.

In an alternative embodiment, demineralized bone sections (approximately 6 bone sections) are combined longitudinally into three small bundles, each having from about 1 to about 3 bone sections. The three bundles are then braided. Various methods of braiding and types of braids any of which may be useful in producing the material of the invention herein are also described, e.g., by Shaw, *KNOTS—Useful & Ornamental*, Bonanza Books, New York (1983), incorporated herein by reference. The ends of the braided demineralized bone section can then be glued together using a fixation agent to prevent their unraveling or they can be held together with a biocompatible polymer or metal band.

In another embodiment, demineralized bone strips can be cut from sheets composed of elongated bone particles, commercially available as GRAFTON® Flex (Osteotech, Eatontown, N.J.) as described, e.g., in U.S. Pat. No. 5,507,813, the contents of which are incorporated by reference herein.

To increase the mechanical strength of bone strips fabricated from bone, chemical linkages can be formed between adjacent bone elements employing, e.g., any of the procedures for accomplishing this disclosed in U.S. Pat. No. 6,123,731, the contents of which are incorporated herein by reference.

Medically/surgically useful substances which promote or accelerate healing can be incorporated in the implant of this invention. Useful substances of this kind which can be incorporated into the implant include, e.g., collagen, insoluble collagen derivatives, etc., and soluble solids and/or liquids dissolved therein, e.g., antiviral agents, particularly those effective against HI and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin, and gentamicin, etc.; biocidal/biostatic sugars such as dextran, glucose, etc.; amino acids; peptides; vitamins; inorganic elements; co-factors for protein synthesis; hormones; endocrine tissue or tissue fragments, synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells; natural extracts; genetically engineered living cells or otherwise modified living cells; tissue transplants; demineralized bone powder (or "demineralized bone matrix" as it may also be referred to); DNA delivered by plasmid or viral vectors; autogenous tissues such as blood, serum, soft tissue, bone marrow, etc.; bioadhesives; bone morphogenic proteins; osteoinductive factor; fibronectin; transforming growth factor-beta; endothelial cell growth factor; cementum attachment extracts; ketaserin; insulin-like growth factor; platelet derived growth factors; epidermal growth factor, interleukin; human alphathrombin; fibroblast growth factors; periodontal ligament chemotactic factor; human growth hormone; animal growth hormone; growth hormones such as somatotropin; bone digesters; antitumor agents; immuno-suppressants; permeation enhancers, e.g., fatty acid ester such as laureate, myristate and stearate monoesters of polyethylene glycol, enamine derivatives, alpha-keto aldehydes, etc.; and, nucleic acids. Preferred biomedically/surgically useful substances are bone morphogenic proteins and DNA delivered by plasmid or viral vector. Suitable methods of incorporation include coating, immersion saturation, packing, co-lyophilization wherein the substance is placed on the bone graft and lyophilized, spraying, injecting, etc. The amounts of medically/surgically useful substances utilized can vary widely with optimum levels being readily determined in a specific case by routine experimentation.

The implant herein can also be fabricated in whole or in part from tendon, ligament and/or small intestine submucosa tissues. These tissues are not osteoinductive but can be made so by incorporating various osteoinductive materials as described above. Tendon tissue useful for fabricating the material includes, but is not limited to, fascia lata, semitendinosus, achilles tendon and patella tendon tissue. Ligament tissue can consist of an entire excised ligament or elongated section thereof. Small intestine submucosa tissue can be obtained and processed as described in U.S. Pat. No. 4,902,508, the contents of which are incorporated by reference herein. The tendon, ligament and small intestine submucosa tissues can be obtained from autogeneic, allogeneic or xenogeneic sources and preferably are obtained from an autogeneic or allogeneic source. The tissues can be excised and cut into a plurality of elongated elements employing methods known in the art. Reduction of the antigenicity of allogeneic and xenogeneic tissue can be achieved by treating the tissues with various chemical agents, e.g., extraction agents such as monoglycerides, diglycerides, triglycerides, dimethyl formamide, etc., as described, e.g., in U.S. Pat. No. 5,507,810, the contents of which are incorporated by reference herein. Medically/surgically useful substances as described above can also be incorporated in or associated with the tendon, ligament and small intestine submucosa tissue as described above with respect to elongated elements obtained from bone.

The implant can also be fabricated from collagen tissue which can be obtained from any autogeneic, allogeneic or xenogeneic source, preferably from an autogeneic or allogeneic source. Collageneous tissue sources include, but are not limited to, skin, tendon, intestine and dura mater obtained from animals, transgenic animals and humans. Collagenous tissue can also be obtained by genetically engineering microorganisms to express collagen as described, e.g., in aforementioned U.S. Pat. No. 5,243,038. Procedures for obtaining and purifying collagen are well known in the art and typically involve acid or enzyme extraction as described, e.g., in U.S. Pat. No. 5,263,984, the contents of which are incorporated by reference herein. Collagen is also commercially available (Pentapharm). The purified collagen is then subjected to further processing to obtain collagen fibers or collagen threads, which can optionally be treated with crosslinking agents, e.g., glutaraldehyde, to improve their strength and/or with various medically/surgically useful substances as described above. The collagen threads can be arranged to form various structures, such as a woven or non-woven fabric, bundle or braid, etc. by various techniques known in the art as described, e.g., in U.S. Pat. Nos. 5,171,273 and 5,378,469, each incorporated herein by reference, to provide the implant of the invention. For example, U.S. Pat. No. 5,171,273 describes the preparation of high-strength collagen fibers by dissolving Type I collagen in dilute hydrochloric acid, extruding the solution into a specific fiber formation buffer to reconstitute the collagen fibers. The reconstituted collagen fibers are subsequently crosslinked with glutaraldehyde or other chemical agents and treatments. The fibers are then processed into woven or non-woven materials.

U.S. Pat. No. 5,378,469 describes methods for the production of high strength collagen threads wherein collagen is extruded into a dehydrating agent, e.g., polyethylene glycol, which has a higher osmotic pressure than that of the collagen solution and a pH from about 5 to 10 which results in the formation of collagen threads. If desired, the collagen threads can be crosslinked using various chemical agents. The collagen threads are then utilized to form braided constructs, plied into yarn, and knitted to provide the implant of this invention.

Various constructs of the elongate elements, fibers and threads can be formed utilizing well known techniques, e.g., braiding, plying, knitting, weaving, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. See, e.g., Mohamed, *American Scienitist*, 78: 530-541 (1990). For example, aforementioned U.S. Pat. No. 5,378,469 describes the braiding of crosslinked and non-crosslinked collagen threads using a harness braiding machine (New England Butt Co., Providence, R.I.). Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of uncrosslinked collagen and two threads of crosslinked collagen.

The elongate particles, fibers, and threads can also be plied into yarns using the same methods and same machinery known to those skilled in the art in plying threads made out of other material, e.g., cotton, polyester, etc. For example, aforementioned U.S. Pat. No. 5,378,469 describes the production of a 60 ply yarn from noncrosslinked collagen threads. Therein, 4 collagen threads were twisted together. Three of the resultant 4-ply strands were then twisted together in the opposite direction, and then 5 of the resultant 12 ply strands were twisted in the opposite direction.

The elongated elements and/or fibers and/or threads and/or braided threads or plied yarns can then be knitted into tubular or flat fabrics by using techniques known to those skilled in the art of producing fabrics manufactured from other types of threads. Various medically/surgically useful substances as described above can be incorporated in, or associated with, the braided, knitted, or woven materials.

The implant can also be fabricated in whole or in part from a synthetic biocompatible bioabsorbable polymer or copolymer, a synthetic biocompatible non-bioabsorbable polymer or copolymer, and combinations thereof. As used herein, "bioabsorbable polymer" refers to a polymer or copolymer which is absorbed by the body. "Non-bioabsorbable polymer" refers to a polymer or copolymer which remain in the body without substantial bioerosion. Examples of synthetic biocompatible bioabsorbable polymers or copolymers include, but are not limited to, poly(lactide), poly(glycolide), poly(epsilon-caprolactone), poly(p-dioxanone), poly(epsilon-caprolactone-co-p-dioxanone) and poly(lactide-co-glycolide) as described, e.g, in U.S. Pat. Nos. 5,705,181 and 5,393,594, each incorporated herein by reference; bioabsorbable block copolymers made of hard phase forming monomers, e.g., glycolide and lactide, and soft phase monomers, e.g., 1,4 dioxane-2-one and caprolactone, as described, e.g., in U.S. Pat. No. 5,522,841, incorporated herein by reference; and natural materials such as cotton, and catgut. Examples of synthetic biocompatible non-bioabsorbable polymers include, but are not limited to, homopolymers and copolymers of polypropylene, polyamides, polyvinylchlorides, polysulfones, polyurethanes, polytetrafluoroethylene, etc. The biocompatible material fabricated from the biocompatible polymer can have incorporated within, or be associated with, osteogenic materials such as demineralized bone particles or demineralized bone powder and medically/surgically useful substances as described above.

The implant can also be fabricated in whole or in part from a synthetic biocompatible, optionally bioabsorbable, ceramic or glass, or biocompatible metal. Examples include fibers of phosphate/silica glasses (bioglass), fibers of calcium phosphate, and metal fibers such as titanium or titanium nickel alloys (shape-memory metals).

In a particularly useful embodiment, the aforementioned material making up the implant can be wrapped with a monolithic piece, e.g., strips or sheets, fabricated from a suitable material that is remodeled by the body and replaced over time with new bone tissue. For example, the material can be wrapped or surrounded with demineralized bone strips cut from sheets which are composed of elongated bone particles, commercially known as GRAFTON® Flex (Osteotech, Eatontown, N.J.) as described, e.g., in aforementioned U.S. Pat. No. 5,507,813.

These demineralized bone strips can be affixed to the biocompatible osteogenic material by any convenient method, e.g., adhering the strips to the material utilizing adhesives, suturing the strips to the biocompatible osteogenic material, braiding the strips around the biocompatible osteogenic material, etc.

The implants of this invention can be utilized in a wide variety of orthopedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, repair of ligaments or tendons in the hand, elbow, knee, foot, ankle or any other anatomical location, etc. These materials can be sutured or stapled in place for anchoring purposes and serve in guided tissue regeneration or as barrier materials.

It will be understood that various modifications may be made to the embodiments disclosed herein. Therefore, the above description should not be construed as limiting, but merely as exemplifications of preferred embodiments. Those skilled in the art will envision other modifications within the scope and spirit of the disclosure herein.

What is claimed is:

1. An implant comprising a quantity of flexible, elongated elements, at least some of which being one or more of filaments, threads, fibers, or strips comprising bone-derived tissue, and at least some of which possess connective tissue-healing activity, substantially all the elements being arranged in a braid, plied thread, spun yarn, or twist in substantially common alignment with a common axis, wherein the elongated elements have been modified at one or both ends to allow for the attachment of bone to the end, wherein the implant is substantially longer than it is wide, and wherein the implant is substantially longer than it is thick, wherein the elongated elements in the form of threads are assembled into yarns and the yarns are assembled into a braid.

* * * * *